US005846581A

United States Patent [19]
Catron

[11] Patent Number: 5,846,581
[45] Date of Patent: Dec. 8, 1998

[54] CHROMIUM (III) SALTS OF SHORT CHAIN FATTY ACIDS COMPOSITION FOR USE IN ANIMAL FEEDS

[76] Inventor: Douglas Howard Catron, 2530 E. 16th St., Des Moines, Iowa 50316

[21] Appl. No.: 792,000

[22] Filed: Jan. 31, 1997

[51] Int. Cl.$^6$ .................................................. A23L 1/304
[52] U.S. Cl. ............................................ 426/74; 426/807
[58] Field of Search ....................................... 426/74, 807

[56] References Cited

U.S. PATENT DOCUMENTS

| | | |
|---|---|---|
| 2,650,239 | 8/1953 | Stover . |
| 2,678,328 | 5/1954 | Drew . |
| 3,755,391 | 8/1973 | Bertrand et al. . |
| 4,101,567 | 7/1978 | Fitzmaurice et al. . |
| 4,315,927 | 2/1982 | Evans . |
| 4,636,572 | 1/1987 | Hudson et al. . |
| 4,700,000 | 10/1987 | Merkel et al. . |
| 4,764,633 | 8/1988 | Anderson et al. . |
| 5,061,815 | 10/1991 | Leu . |
| 5,336,672 | 8/1994 | Southern, Jr. et al. . |
| 5,487,772 | 1/1996 | McCoy ...................................... 426/74 |
| 5,591,878 | 1/1997 | Nelson et al. . |

OTHER PUBLICATIONS

Schwarz and Mertz, "Chromium (III) and the Glucose Tolerance Factor", *Journal of the National Institutes of Health,* Aug. 6, 1959.

Katz, Sidney A. and Harry Salem. *The Biological and Enviromental Chemistry of Chromium.* New York: VCH Publishers, Inc., 1994.

"Trivalent Chromium and Glucose Tolerance", *Nutrition Reviews,* vol. 19, No. 11, Nov. 1961.

"GTF chromium benefits stressed feeder calves", *Journal of Animal Science,* vol. 69, supplement 1, 1991.

Mertz, Walter, "Chromium Ocurrence and Function in Biological Systems", *Physiological Reviews,* vol. 49, No. 2, Apr. 1969.

*Chromium,* vol. 1, ed. Udy, A.C.S. Monograph Series No. 132, Reinhold, NY, 1956.

*Concepts and Models of Inorganic Chemistry,* $2_{nd}$ Edition, ed. Douglas. New York: John Wiley & Sons, Inc., 1983.

*The CRC Handbook of Chemistry and Physics,* $55^{th}$ Edition, ed. Robert C. Weast, Ph.D. Cleveland, OH: CRC Press, 1974.

*The CRC Handbook of Biochemistry,* $2^{nd}$ Edition, ed. Herbert A. Sober, Ph.D. Cleveland, OH: The Chemical Rubber Co., 1970.

*Advanced Inorganic Chemistry: A Comprehensive Text,* $3^{rd}$ Edition ed. F. Albert Cotton. New York: Interscience Publishers, 1972.

Mertz, Roginski, and Schwarz, "Effect of Trivalent Chromium Complexes on Glucose Uptake by Epididymal Fat Tissue of Rats", *Journal of Biological Chemistry,* vol. 236, No. 2, Feb. 1961.

McDowell, Lee Russell. *Minerals in Animal and Human Nutrition.* San Diego, CA: Academic Press, Inc., 1992.

Lindemann, M.D. "Current Understanding of Chromium Use in Practical Swine Diets", pp. 223–233, 57th Minnesota Nutrition Conference and Protiva Technical Symposium; Sep. 23–25, 1996.

*Primary Examiner*—Helen Pratt
*Attorney, Agent, or Firm*—Kent Herink; Dana Rewoldt

[57] ABSTRACT

The present invention relates to metal carboxylates and more particularly to chromium(III) and manganese(II) salts of short chain fatty acids. A method of making the same such that there are only sub part per billion amounts of these metals in other valent forms present in the resultant salts, and the salts are suitable for use as nutritional supplementation of living organisms with the organic metal salts.

2 Claims, No Drawings

CHROMIUM (III) SALTS OF SHORT CHAIN FATTY ACIDS COMPOSITION FOR USE IN ANIMAL FEEDS

FIELD OF THE INVENTION

The present invention relates to metal carboxylates and, more particularly, to chromium(III) and manganese(II) salts of short chain fatty acids. A method of making the same, such that there are only sub-part-per-billion amounts of these metals in other valent forms present in the resultant salts, and the salts are suitable for use as nutritional supplementation of living organisms with the organic metal salts.

BACKGROUND AND PRIOR ART

Trace metals appear to be essential elements in the diet of living organisms, necessary to promote good health and the proper function of many biochemical enzymatic reactions and transportation processes. Since food intake does not always supply the appropriate amounts of these trace metals, such as chromium, iron, copper, zinc, manganese, etc., dietary supplementation is used. This is not only true for humans but also for animals. The supplemental material provides trace metals in several forms, including the inorganic salts of the trace metals, metal amino acid complexes, metal-amino acid chelate complexes, metal proteinate complexes and metal polysaccharide complexes.

The bioavailability of these trace metals differs which affects the amount of trace metal that is actually assimilated by the organism. Certain of these trace metal compounds have been approved for the use in agricultural animal feed supplements. One of the most recent approvals has been for the supplementation of chromium in animals by providing chromium as chromium picolinate. However, the presently available forms of bioavailable chromium, such as chromium picolinate or chromium yeast, appear to evidence ~12 ppb of chromium (VI). Chromium (VI) has not been approved for addition to agricultural animal feed and may actually be potentially harmful as an animal waste product and detrimental to the animals' overall health.

Chromium (III) is a trace metal that contributes to carbohydrate, insulin, and protein processes in the body. Manganese (II) is associated with a number of enzymatic reactions, including those contributing to growth and maintenance of bone and connective tissue. According to a number of animal studies, supplementation to animal feed with these trace metals provides health benefits to agricultural animals such as swine, beef and poultry. The effect of chromium (III) in a diet has been investigated in several animal species. Particularly, it has been shown in several studies to improve daily gain in swine and pigs per litter in sows. It has been theorized that the effect of chromium is due to an interaction with insulin which allows the metabolism of energy to take place more efficiently.

As noted, it has been found that the addition of chromium (III) to a diet can increase the utilization of energy in the diet by the animal. However, the chromium is only a benefit to the diet if the chromium is bioavailable. It is noted that inorganic forms of chromium have very little biological activity, and that chromium (VI) is both an inactive form of chromium as well as being toxic and carcinogenic (McDowell). It is also noted that chronic exposure to even trace levels of chromium (VI) increase rates of carcinoma.

Most of the processes in the prior art for converting Chromium III to a bioavailable supplement source for feed use chromium (III) as the staring material. However, a few industrial processes use chromium (VI) as the starting material to get a chromium (III) resultant material. Although not a process that could be used to make a chromium compound usable as a dietary supplement, there are some processes for converting valence +6 chromium into valence +3 chromium for industrial purposes, such as for use in oil production (U.S. Pat. No. 4,636,572). Another process for the industrial production of chromium(III) short chain fatty acids has been developed and described in U.S. Pat. No. 2,678,328 to Drew (hereinafter the '328'). In this process, a dichromate salt is reduced with glycolic acid in the presence of the fatty acid to produce the chromium(III) fatty acid salt. To make the process work, Drew implemented a process of flow injection of the reducing agent into a fast-moving chromium stream and (according to column two lines 45–55) attempted to run the initial reaction mixture at less than 10 percent by weight of water.

Unfortunately, these chromium salts produced by this process are unacceptable for use in animal feed. Glycolic acid is not recognized as a feed ingredient by the FDA. Residues of glycolic acid would exclude these salts from such use. Glycolic acid is also found to be a poor reagent in this process, because the reagent grade acid contains between thirty and forty three percent water. It is known that water in the reaction mixture of the process of Drew causes the reaction to not proceed to completion (U.S. Pat. No. 2,615,031 to Stover). The amount of water added to the reaction mixture with the glycolic acid would be small, but it may still result in increased chromium(VI) residues in the product. While this amount of residue may be acceptable in industrial grade products, this is not believed acceptable in a product developed for internal use by humans and animals. In fact, McDowell, in a book entitled "Minerals in Animal and Human Nutrition, pp. 368–70 published by Academic Press in 1992, notes that chronic exposure to even trace levels of chromium(VI) increase rates of carcinoma. Similarly, Manganese (VII) is considered the less healthy form of the trace mineral. The desirable form for diet supplementation is manganese (II).

Ed. Udy, in an A.C.S. Monograph Series no. 132 entitled Chromium Vol. 1, indicates that several other reducing agents may be used to reduce dichromate salts to chromium (III) acetates. At least one of this list is less problematic than glycolic acid, that being glucose. However, he does not give any indication of the extent to which such a reaction would proceed, nor does Udy specify which of many forms of chromium(III) acetate cited would be formed by such a reaction. Further, Udy states that these compounds are not "simple". In fact, he cites that some forms of the acetate are only slightly soluble in water. Low solubility may be an indication of lower bioavailability, thus leading to a conclusion that this type of reaction would not be suitable for formation of a chromium compound that would be useful as a nutritional diet supplement.

There remains a need for a process of preparing a Chromium (III) and a Manganese (II) salt of a short chain fatty acid that is substantially pure of any unreduced Chromium (VI) and any Manganese (VII), respectively. Additionally, there remains a need for a process that reduces Chromium (III) and a Manganese (II) from the respective +6 and +7 valence form, uses a reducing agent that is acceptable for feeding to animals or humans, and contains the Chromium (III) and a Manganese (II) in a bioavailable form. Still further, there is a need for a chromium (III) organic salt that is substantially pure of hexavalent chromium.

SUMMARY OF THE INVENTION

The discovery relates to a process for producing a substantially pure (herein after defined as containing only undetectable amounts of the unreduced metal ($Cr^{+6}$) or ($Mn^{+7}$), respectively) trivalent ($Cr^{+3}$) or divalent ($Mn^{+2}$) salt of a carboxylic acid (a metal carboxylate) having a formula of $M(CH_3 (CH_2)_x COO^-)_y$, where M is the trivalent or divalent metal cation, manganese ($Mn^{+2}$) or chromium ($Cr^{+3}$) and x is zero or one or two or three or four, and preferably zero or one so that an acetate or propionate salt is made, and y is an integer equal to the cationic charge of M. The following discussion will focus on the ($Cr^{+3}$) use, but it should be understood that, taking into account the valence differences, this process should work equally as well with ($Mn^{+2}$). The discovered process begins with the mixing of 1) a carboxylic acid of $C_2$–$C_6$ and preferably $C_2$–$C_3$ with: 2) a polyvalent metal (polyvalent shall be defined here to be valences of greater than +3 valence) of a metal selected from chromium(VI) or manganese(IV) as a salt; and, 3) adding "selected reducing agents", herein after defined as reducing agents that pass the three part test: a) the reducing agent must be able to drive the reaction to completion, b) reducing agent does not leave any residues that would be toxic when fed to the targeted biological organism; c) the excess reducing agent in the final product is acceptable at the levels found to be in the feed of the organism which is targeted to consume it. The answer to these three questions can be determined without undue experimentation by those of skill in the art. The preferred reducing agents are glucose or propylene glycol, resulting in a metal salt of a short chain fatty acid with substantially no Chromium (VI) present in the resultant material. More particularly, the process of the present invention is the preparation of chromium (III) propionate by the reduction of sodium dichromate dihydrate with propylene glycol, or other suitable reducing agent, in the presence of propionic acid.

Herein, the term feed stuff is used to describe a mixture of plant or animal material, such as grain or animal by-products, vitamins, minerals or other feed additive used to feed agricultural or domesticated animals. The term food stuff is used to describe any item which may be consumed by humans. The term food is defined as all food stuffs and feed stuffs.

DESCRIPTION OF THE INVENTION

The discovered process results in a bioavailable chromium metal salt of a fatty acid which has undetectable amounts of chromium (VI) (less than 6 ppb). This is in contrast with the presently available forms of bioavailable chromium, such as chromium picolinate or chromium yeast, that evidence at ~12 ppb of chromium (VI). The discovered process begins with the mixing of 1) a carboxylic acid of $C_2$–$C_6$ and preferably $C_2$–$C_3$ with: 2) a polyvalent metal (polyvalent shall be defined here to be valences of greater than +3 valence) selected from chromium(VI) or manganese (IV) as a salt; and 3) adding "selected reducing agents", hereinafter defined as reducing agents that pass the three part test a) the reducing agent must be able to drive the reaction to completion (preferably in less than 24 hours); b) the reducing agent does not leave any residues that would be toxic when fed to the targeted biological organism (particularly humans or agricultural animals); c) the excess reducing agent in the final product is acceptable at the levels found to be in the feed of the organism which is targeted to consume it. The preferred reducing agents are glucose or propylene glycol. The process results in a metal salt of a short chain fatty acid with substantially no Chromium (VI) or polyvalent metal present in the resultant material.

To determine if the reaction is driven to completion, the reaction may be tested for the presence of the polyvalent metal; if that metal is not present, then the reduction is complete. Alternatively, excess amounts of the reducing agent can be used to assure reduction. Residues can be tested by spectographic analysis of the resultant material and comparison with the targeted organisms' tolerance for the residue; or, alternatively, the material can be fed to animals in control studies to determine the toxicity. The last test can be readily established by referencing approved materials for foods or for feeds; alternatively, controlled animal studies can be run on the target animal. Thus, in producing the chromium (III) salt of the fatty acid acetate or propionate, several components are used: 1) a chromium (VI) component, 2) an anhydrous short chain fatty acid, and 3) a reducing agent.

The molar ratio of fatty acid to chromium(VI) should be 3:1; however, additional propionate may be added as solvent. The reducing agent must be adding in amounts sufficient to drive the reaction to completeness, and, if the reducing agent is the preferred propylene glycol, then there should be approximately 0.4 moles per mole of chromium (VI).

Chromium(VI) Component

The chromium (VI) component is selected from any of the alkali metal or alkali earth metal or ammonium dichromates or chromate. Such salts would have the form of $M_x(Cr_2O_7)_y$, or $M_x(CrO_4)_y$, where M is any cation, and x and y are such that the charges of the cations and anions are equal. These salts may be in any hydrous or anhydrous form.

Presently, the preferred is sodium or potassium dichromate dihydrate, because of cost and ease of accessibility. There is no particular difference whether chromate or dichromate is used, since in acid, the chromate converts. However, when chromate is used, additional propionic (or other fatty acid selected) may be required.

Fatty Acid Selection

The fatty acid component is selected based on its having a formula of at least stoichmetric amounts, and preferably excess stoichmetric amounts, of the following: ($CH_3 (CH_2)_x COOH$), where x is zero or one or two or three or four, used to form a trivalent ($Cr^{+3}$) or divalent ($Mn^{+2}$) salt of a carboxylic acid (a metal carboxylate). Preferably, x=zero or one, so that an acetate or propionate salt is made, and the number of these acids per each metal is an integer equal to the cationic charge of M (the metal). Carboxylic acids of $C_2$–$C_6$ are acetate, propionate, butyrate, and valerate respectively. Valerate is the least preferred. Preferably $C_2$–$C_3$ acetate and propionate are used, as they evidence fewer undesirable traits for the consummation of the final product. The fatty acids are preferably in the neat or anhydrous form to avoid addition of water to the reaction. Water makes the reaction more susceptible to having undesirable polyvalent metals in the resultant material.

Reducing Agent Selection

"Selected reducing agents" are defined as reducing agents that pass the three part test: a) the reducing agent must be able to drive the reaction to completion (preferably in less than 24 hours); b) reducing agent does not leave any residues that would be toxic when fed to the targeted biological organism (particularly humans or agricultural animals); c) the excess reducing agent in the final product is acceptable at the levels found to be in the feed of the organism which is targeted to consume it. The preferred reducing agents are glucose or propylene glycol; however, it is thought that other mono, di or poly-saccharides such as fructose or sucrose may also act as adequate reducing agents for the purposes of this reaction. Likewise, other glycols may be useful if they pass the three-part test. Once the three part test is passed by a reducing agent, then the researcher should evaluate the selected reducing agents based on availability, price, and where the metal is being over-reduced. For example, glucose is less preferred than propylene glycol, because glucose can turn brown and form Chromium (II) which, in the oxidized form, is totally non-bioavailable to animals.

After all of the reactants/reagents have been admixed together, a sufficient time should be allowed for the reaction to reach completion. The reaction temperature should be under control to avoid excessive heat from this exothermic reaction. Presently suggested are reaction times of twenty minutes to 24 hours, the preferred range being 1–3 hours. The reaction temperatures should be about 60 degrees C.–120 degrees C. Times greater than 24 hours can be employed, but they do not appear to be necessary, as the reaction goes to completion fairly rapidly. The product of this reaction is a solution of Chromium (III) in propionic acid. This mixture can be directly added to feed or sprayed on plant material or, alternatively, made into a dry form by adding a carrier such as silicon dioxide, cobmeal, calcium carbonate, vermiculite, bentonite and the like.

EXAMPLES

Examples provided are intended to assist one skilled in the art in a further understanding of the invention. The materials employed are not limitations, but rather exemplary. The specification, text, examples, data and claims should be viewed as a whole in considering the scope of the invention.

Chromium(III) propionate was synthesized by the following reaction. In the laboratory runs a variable speed mechanical stirrer, a water cooled reflux condenser and a probe for determining the temperature of the reaction may have been employed. Heat was added where necessary by a heating unit.

Example 1

Propionic acid and sodium dichromate were mixed in a reaction vessel. The reaction mixture was heated to 90° C. Glucose was added in small portions to the reaction mixture. Several seconds after each addition, large amounts of gas were produced by the mixture, and the temperature of the mixture increased sharply to ~120°–135° C. Propionic acid vapor was refluxed back into the vessel using a water cooled condenser. Portions of glucose were added until the reaction had gone to completion. The reaction time was ~3 hours, but the time was dependent on how quickly the glucose is added. If the glucose were added in one portion, the reaction was complete within minutes. Upon further experimentation, it was found that the reaction was very slow until the reaction mixture was heated to 85°–90° C. It was also found the optimum ratio of sodium dichromate to glucose was 5.8 to 1 weight to weight; however, more glucose may be added to ensure complete reaction. It was also found that the minimum amount of propionic acid to sodium dichromate was 6 to 1 on a mole basis. More than this amount of propionic acid was used in the laboratory reactions to act as a solvent. A solvent is necessary in the reaction to ensure that the glucose can properly react with the chromium(VI). It is thought that other non-water containing solvents or mixtures of solvents may be used in this reaction, as long as they do not interfere with the reaction, and any residues present in the final product are acceptable and pass the three part test above. Glucose was used in this experiment. However, it is possible that other mono, di or poly-saccharides such as fructose, sucrose, dextrose, or corn or table sugar, may also act as an adequate reducing agent for the purposes of this reaction. Other chromium(VI) containing salts may be used for the purposes of this reaction. Such salts would have the form of $M_x(Cr_2O_7)_y$ or $M_x(CrO_4)_y$ were M is any cation and x and y are such that the charges of the cations and anions are equal. These salts may be in any hydrous or anhydrous form.

Example 2

The same experiment, as outlined in example one, was run; the changes to the experiment are noted herein. Propylene glycol could also be used as a reducing agent in place of the glucose. 499.73 g propionic acid, 166.58 g sodium dichromate, and 33.55 g propylene glycol were reacted in a similar manner to the reaction above. The product was identical to that of the reaction using glucose as the reductant. Similarly to glucose, propylene glycol is acceptable as a feed additive.

The particular product of these reactions was found to be dark green and very viscous. Upon drying, the product solidified and turned to a medium green. The product was found to be very soluble in water and contain only trace amounts of chromium(VI).

Example 3

The same experiment, as outlined in example one, was run; the changes to the experiment are noted herein. 382.07 g of $Na_2Cr_2O_7H_2O$, 66.24 g dextrose, and 1146.2 grams of propionic acid were allowed to react. After the reaction ran, 1146 grams (1:1 ratio to grams of acid) of Sipernat (silicon dioxide) was added. The material was made as three separate batches, and was used to determine bioavailability of the chromium to animals in example 7.

The particular product of this reaction has since been found to be bioavailable. No further purification of the product is necessary before it is acceptable to be fed to animals as a supplement.

Example 4

The three factors in the study will be feed energy, chromium level, and propionate level. The responses in this study will be eggs per hen per day, egg mass per hen per day, and feed intake per hen per day. From this data, feed-to-egg mass conversion will also be calculated.

A high energy level feed at 1376 kcal/LB and a low energy level feed at 1097 kcal/LB were formulated per the guidelines in Feed & Nutrition by Ensminger and Olentine, first edition. The two formulations were balanced for crude protein, methionine, and lysine content. The two formulations are listed in Table 1.

TABLE 1

| Ingredient | High Energy Diet | Low Energy Diet |
|---|---|---|
| Corn Meal | 64.00% | 56.00% |
| Soybean Meal | 0.00% | 16.00% |
| Corn Gluten Meal | 4.00% | 4.00% |
| Meat and Bone Meal | 17.00% | 14.50% |
| Poultry Fat | 5.50% | 0.00% |
| Calcium Phosphate | 1.00% | 1.00% |

TABLE 1-continued

| Ingredient | High Energy Diet | Low Energy Diet |
| --- | --- | --- |
| Limestone | 7.31% | 7.42% |
| Salt | 0.30% | 0.30% |
| L-Lysine | 0.15% | 0.05% |
| DL-Methionine | 0.16% | 0.15% |
| Trace Mineral Premix | 0.08% | 0.08% |
| Vitamin Premix | 0.50% | 0.50% |

The high chromium level will be 500 ppb. No adjustment is necessary for the low level because only 5.67 g of an 8% chromium product will treat one ton of feed at 500 ppb. The high level of propionate will be one percent calcium propionate to the feed. One percent calcium carbonate will be added to the low propionate level treatment to keep the treatments balanced.

The eight treatments are listed in Table 2.

TABLE 2

| Treatment | Energy | Chromium | Propionate |
| --- | --- | --- | --- |
| 1 | High | High | High |
| 2 | High | High | Low |
| 3 | High | Low | High |
| 4 | High | Low | Low |
| 5 | Low | High | High |
| 6 | Low | High | Low |
| 7 | Low | Low | High |
| 8 | Low | Low | Low |

Each of the eight treatments will be fed to three randomly selected pens of eight or nine birds. The trial will last for 5 weeks. The hens will be given feed and water ad libitum for the duration of the trial. Feed intake and eggs per hen per day will be recorded daily throughout the trial. During the last five days of the trial the weight of each days egg production will be recorded for each pen. The results of this study indicates the effect of bioavailable chromium on poultry.

Example 5

The same experiment, as outlined in example 3, was run; the changes to the experiment are noted herein. When large excesses of glucose were added to the reaction mix, the product turned brown. This was due to the conversion from chromium(III) salts to chromium(II) salts. These salts are known to have equal efficacy to chromium(III) salts (McDowell). However, due to the fact that they are unstable in air, they are not suitable for use in animal feeds. As the chromium(II) oxidizes it may form chromium(III) oxide, which is completely biologically inert.

Example 6

Ion chromatography, using EPA method 218.6, was used to analyze a sample of chromium propionate prepared in the lab from sodium dichromate and a sample of Chromax—10X (0.4% chromium picolinate). The analysis was done using Dionex equipment. No residual chromium(VI) could be detected in our product with a detection limit of 8.3 ppb, while chromium picolinate was found to contain 13 ppb. It must be noted that our product contained about 20 times the chromium of chromium picolinate. On an equal chromium basis, our product contain at least an order of magnitude less chromium(VI). A sample of high chromium yeast was also analyzed and found to contain 600 ppb chromium(VI).

Example 7

An experiment using the materials from experiment in Example 3 was run to determine the effects of dietary chromium tripicolinate (Cr Plc) and chromium propionate (Cr Prop) on swine growth, blood metabolites, glucose tolerance, and insulin sensitivities. 36 swine in three groups of 12, initial barrow weight 20.2 and 38.4 kg, were used in the study. The following feeds were used: corn-soybean meal basal (control), the control feed plus 200 ppb chromium as Cr Plc test 1, the control feed plus 200 ppb chromium as Cr Prop test 2. Data on swine growth was gathered for 28 days; then 23 of the 24 pigs were fitted with catheters and a glucose tolerance and insulin challenge data were gathered. Both test 1 and 2 decreased $P<0.05$ average daily gain and average feed intake per day, but not feed efficiency($p>0.10$). Plasma from fasting swine showed neither source affected total cholesterol, urea, insulin, or HDL totals. Test 1 showed higher HDL concentrations tended to be higher for test 1 ($p=0.12$) than test 2 pigs; pigs in test one had decreased ($p<0.02$) fasting plasma non-esterified fatty acid concentrations and pigs in test two tended ($p=0.12$) to have lower non-esterifed fatty acid concentration than control pigs. During the insulin challenge, glucose clearance was increased ($p<0.01$) in pigs in test two and tended to be increased ($p=0.12$) in pigs in test one. Glucose half-life was decreased by both tests. Both sources of organic chromium affect metabolism in pigs.

The animal experiments show that chromium propionate made by this process positively affects the metabolism of animals and shows similar, if not better, results than does chromium picolinate.

It is understood that the foregoing detailed description of the invention is merely illustrative and that modifications and variations are within the scope of the invention.

I claim:

1. A food composition for selectively supplementing essential trace metals in a diet comprising:

a food composition including a $Cr^{+3}$ salt of a carboxylic acid, and low levels of $Cr^{+6}$; and, said low levels of $Cr^{+6}$ in said food composition having the equivalent of less than 8.3 parts per billion of $Cr^{+6}$ per 8% total chromium in the food composition.

2. A food composition according to claim 1 wherein the carboxylic acid is selected from a group consisting of: acetate, propionate, and picolinate.

* * * * *

UNITED STATES PATENT AND TRADEMARK OFFICE
CERTIFICATE OF CORRECTION

PATENT NO. : 5,846,581
DATED : December 8, 1998
INVENTOR(S) : Catron

It is certified that error appears in the above-identified patent and that said Letters Patent is hereby corrected as shown below:

Title page,
Item [56], References Cited, OTHER PUBLICATIONS, "Schwarz and Mertz, "Chromium (III) and the Glucose tolerance Factor", *Journal of the National Institutes of Health*, Aug. 6, 1959" change to -- Schwartz, K., and Mertz, W., "Chromium (III) and the Glucose Tolerance Factor", *Archives of Biochemistry and Biophysics*, 75, 292-95 (1959). --

Signed and Sealed this

Eleventh Day of January, 2005

JON W. DUDAS
*Director of the United States Patent and Trademark Office*